(12) United States Patent
Gaffney et al.

(10) Patent No.: US 11,786,511 B2
(45) Date of Patent: Oct. 17, 2023

(54) METHODS FOR INCREASING CIRCULATING MESENCHYMAL STEM CELLS

(71) Applicants: Kevin J. Gaffney, Los Angeles, CA (US); Kathleen E. Rodgers, Los Angeles, CA (US); Maira Soto, Los Angeles, CA (US); Michael Weinberg, Los Angeles, CA (US)

(72) Inventors: Kevin J. Gaffney, Los Angeles, CA (US); Kathleen E. Rodgers, Los Angeles, CA (US); Maira Soto, Los Angeles, CA (US); Michael Weinberg, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 169 days.

(21) Appl. No.: 16/638,000

(22) PCT Filed: Aug. 9, 2018

(86) PCT No.: PCT/US2018/045935
§ 371 (c)(1),
(2) Date: Feb. 10, 2020

(87) PCT Pub. No.: WO2019/036267
PCT Pub. Date: Feb. 21, 2019

(65) Prior Publication Data
US 2020/0215037 A1 Jul. 9, 2020

Related U.S. Application Data

(60) Provisional application No. 62/546,256, filed on Aug. 16, 2017.

(51) Int. Cl.
| | | |
|---|---|---|
| *A61K 31/427* | (2006.01) | |
| *A61K 31/4439* | (2006.01) | |
| *A61K 31/496* | (2006.01) | |
| *A61K 31/5377* | (2006.01) | |
| *A61K 45/06* | (2006.01) | |

(52) U.S. Cl.
CPC ........ *A61K 31/427* (2013.01); *A61K 31/4439* (2013.01); *A61K 31/496* (2013.01); *A61K 31/5377* (2013.01); *A61K 45/06* (2013.01)

(58) Field of Classification Search
CPC .............. A61K 31/427; A61K 31/4439; A61K 31/496; A61K 31/5377; A61K 45/06; A61K 38/18; A61K 31/395; A61P 3/10; A61P 7/06; A61P 9/00; A61P 9/10; A61P 13/00; A61P 17/00; A61P 17/06; A61P 21/00; A61P 21/04; A61P 25/16; A61P 1/16; A61P 11/00; A61P 19/02; A61P 25/28; A61P 27/02; A61P 43/00
See application file for complete search history.

(56) References Cited

U.S. PATENT DOCUMENTS

| | | | | |
|---|---|---|---|---|
| 2009/0054342 A1* | 2/2009 | Cohen | ............ | A61P 35/00 530/387.9 |
| 2016/0016946 A1 | 1/2016 | Petasis et al. | | |

OTHER PUBLICATIONS

Zang et al (J Clin Endocrinol Metab 96:320-332, 2011) (Year: 2011).*
Choi (Int J Stem Cells 2(2):122-128, 2009) (Year: 2009).*
Kalodimou (J Autoimmune Disorders, 1(1:8):pp. 1-3, 2015) (Year: 2015).*
Xu et al (J Orthopaedic Translation 2:1-7, 2014) (Year: 2014).*
The International Search Report (ISR) with Written Opinion for PCT/US2018/045935 dated Oct. 31, 2018, pp. 1-13.

* cited by examiner

*Primary Examiner* — Craig D Ricci
(74) *Attorney, Agent, or Firm* — McDonnell Boehnen Hulbert & Berghoff LLP

(57) ABSTRACT

Disclosed herein are methods for increasing circulating mesenchymal stem cells by administering a compound having the general formula 1 as defined herein, or a pharmaceutically acceptable salt thereof.

7 Claims, 1 Drawing Sheet

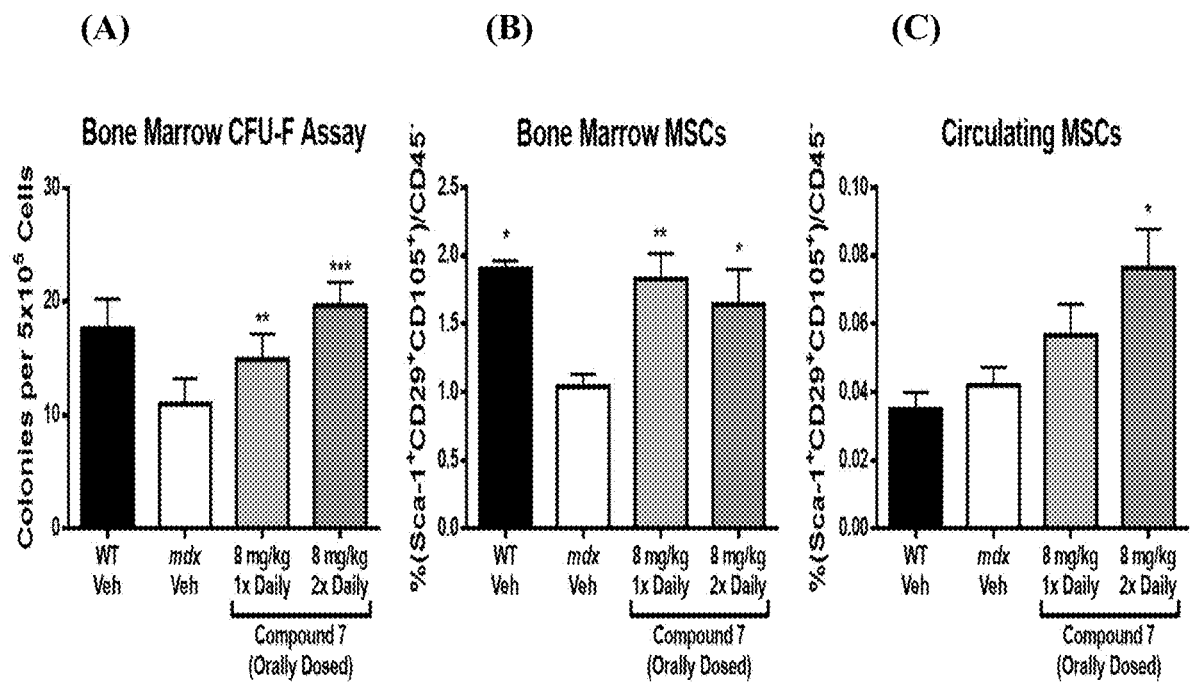

METHODS FOR INCREASING CIRCULATING MESENCHYMAL STEM CELLS

CROSS REFERENCE

This application is a U.S. national phase of International Application No. PCT/US2018/045935, filed on Aug. 9, 2018, which claims priority to U.S. Provisional Application No. 62/546,256, filed Aug. 16, 2017, both of which are incorporated by reference herein in their entirety.

FEDERAL FUNDING STATEMENT

This invention was made with government support under MD 140084, awarded by the (DoD) US Department of Defense. The government has certain rights in the invention.

BACKGROUND

Mesenchymal stein cells (MSCs) are multipotent progenitor cells of the mesoderm capable of differentiating into a number of different cells types including osteoblasts, chondrocytes, myocytes, and adipocytes, implicating their potential to regenerate bone, cartilage, muscle, and fat, respectively. MSCs also have potent anti-inflammatory and immunomodulatory properties. As a result of both of these capacities, MSCs are under clinical development for wide range of conditions including, but not limited to: myocardial infraction, graft versus host disease, diabetes, liver cirrhosis, spinal cord injury, osteoarthritis, Crohn's disease, multiple sclerosis, aplastic anemia, systemic lupus erythematosus, rheumatoid arthritis, Parkinson's disease, brain injury, and muscular dystrophy. In these clinical programs, MSCs are sourced from fetal or adult tissue, potentially expanded in culture, and injected or infused into the patient. When administered intravenously, MSCs become trapped in the lung limiting the systemic exposure. An orally dosed agent that can stimulate to proliferation of MSCs and increase circulating MSCs would represent an exciting alternative approach to accessing these therapeutically powerful cells.

SUMMARY

In one aspect methods for (a) increasing circulating mesenchymal stein cells (MSC) in a subject, or (b) treating a subject having a disorder selected from the group consisting of myocardial infraction, cardiovascular disease, graft versus host disease, diabetes, liver cirrhosis, liver disease, spinal cord injury, osteoarthritis, Crohn's disease, multiple sclerosis, aplastic anemia, rheumatoid arthritis, autoimmune disorders including alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barré syndrome, idiopathic thrombocytopenic purpura, myasthenia gravis, pemphigus/pemphigoid, pernicious anemia, polyarteritis nodosa, polymyositis, primary biliary, cirrhosis, psoriasis, scleroderma/systemic sclerosis, Sjögren's syndrome, some forms of thyroiditis, some forms of uveitis, vitiligo, granulomatosis with polyangiitis (Wegener's), organ transplantation, organ rejection, Parkinson's disease, neurodegenerative disorders, amyotrophic lateral sclerosis, Alzheimer disease, brain injury, and inflammatory lung disease, are disclosed, comprising administering to subject in need thereof an amount effective to treat the disorder of a compound having the general formula 1 or a pharmaceutically acceptable salt thereof:

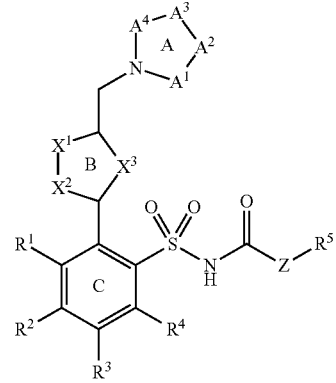

wherein:

ring A is a five-membered or six-membered heteroaryl or heterocyclyl ring containing either a combination of two non-adjacent nitrogen or oxygen atoms, or a combination of three or four nitrogen or oxygen atoms;

ring B is a five-membered or six-membered heteroaryl ring that contains at least one nitrogen atom;

$A^1$, $A^2$, $A^3$, $A^4$ are independently selected from a group consisting of =N—, —C(=O)—, —C($R^a$)=, =C($R^b$)—, —C($R^c$)($R^d$)—N($R^e$)—, —C($R^c$)($R^d$)—O—, and —[C($R^c$)($R^d$)]$_n$—, wherein n is 1 or 2;

$X^1$—$X^2$ is —($R^6$)C—N—, —N—C($R^6$)—, —N—N—, —N—O—, —O—N—, —N—S— or —S—N—;

$X^3$ is —($R^7$)C=C($R^8$)—, —O—, —S—, or —N($R^9$)—;

Z is —O—, —N(H)— or a bond to $R^5$;

$R^a$ and $R^b$ are independently selected from the group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy, or $R^a$ and $R^b$ can also join to form a ring of up to 6 atoms;

$R^c$ and $R^d$ are independently selected from a group consisting of hydrogen, alkyl, aryl, or heteroaryl, provided that $R^c$ and $R^d$, together with the atoms to which they are attached, form a ring of up to 6 atoms;

$R^e$ is hydrogen, alkyl, aryl, heteroaryl, acyl, alkoxyacyl, aminoacyl, dialkylaminoacyl, or dialkylaminoacyl;

$R^1$, $R^3$, $R^4$, $R^6$, $R^7$, and $R^8$ are independently selected from a group consisting of hydrogen, alkyl, alkenyl, alkynyl, aryl, heteroaryl, arylmethyl, heteroarylmethyl, fluoro, chloro, bromo, iodo, cyano, hydroxy, amino, alkylamino, alkoxy, aryloxy, alkoxyalkyl and aryloxyalkyl;

$R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl;

$R^5$ is alkyl, aryl, heteroaryl, hydroxyalkyl, carboxyalkyl, alkoxyalkyl, or aryloxyalkyl; and $R^9$ is hydrogen, alkyl, aryl, heteroaryl, acyl, alkoxyacyl, aminoacyl, dialkylaminoacyl, or dialkylaminoacyl.

In one embodiment, ring A is selected from the group consisting of:

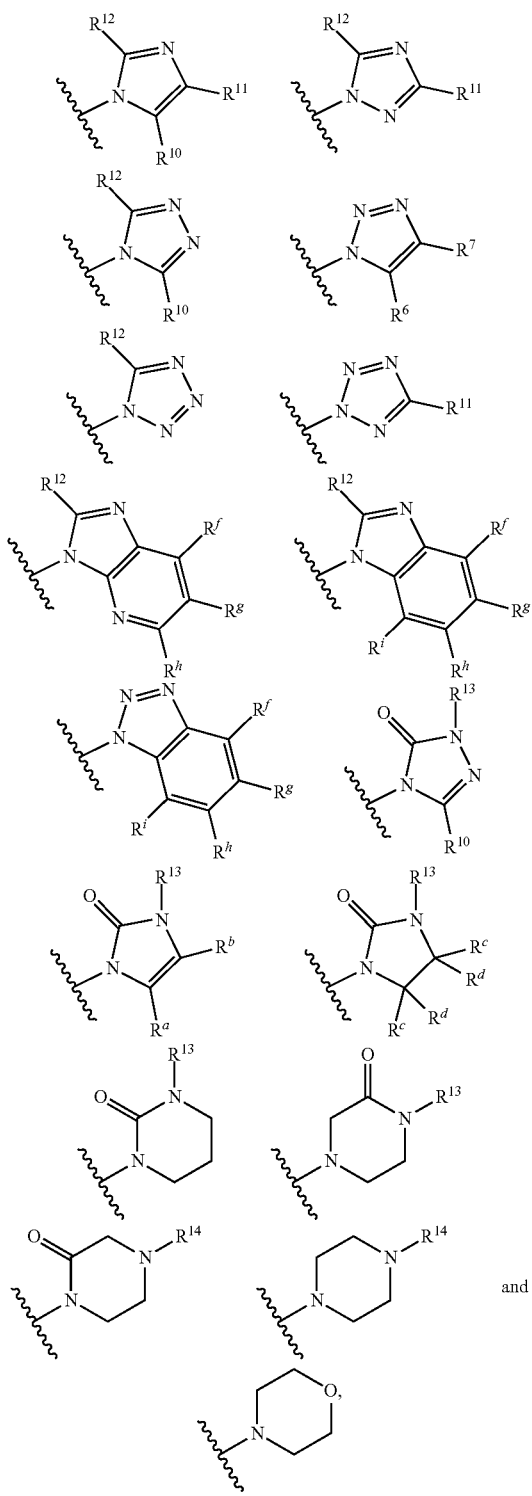

wherein:

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy, or $R^{10}$ and $R^{11}$, together with ring A to which they are attached, form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^{f}$, $R^{g}$, $R^{h}$, and $R^{i}$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl;

or a pharmaceutically acceptable salt thereof.

In another embodiment, ring B is selected from the group consisting of:

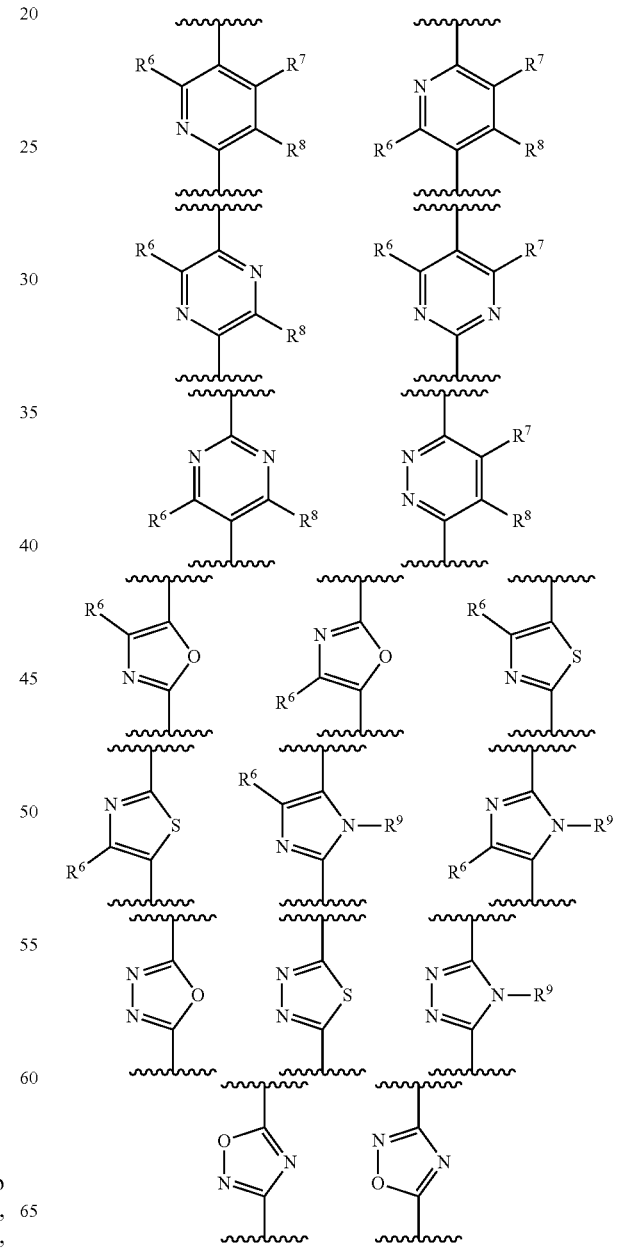

-continued
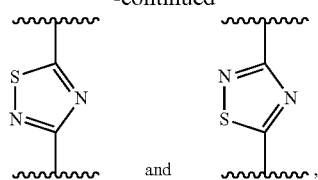
wherein groups $R^6$, $R^7$, $R^8$ and $R^9$ are defined as in general formula 1;
or a pharmaceutically acceptable salt thereof.
In a further embodiment, the compound is selected from the group consisting of:
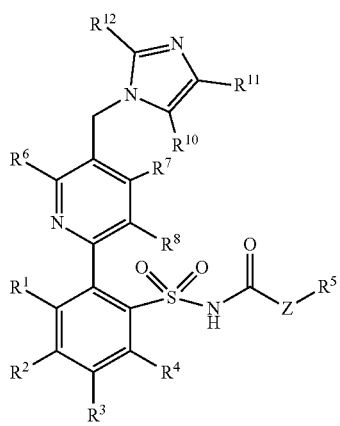
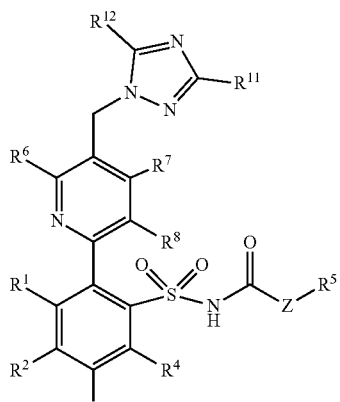
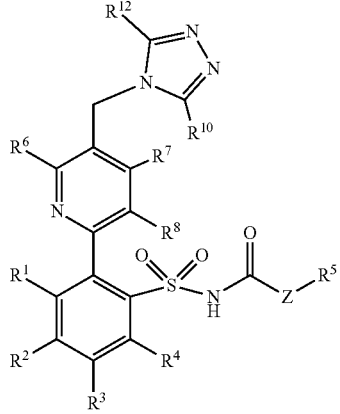
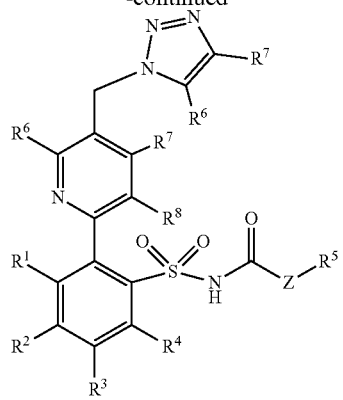
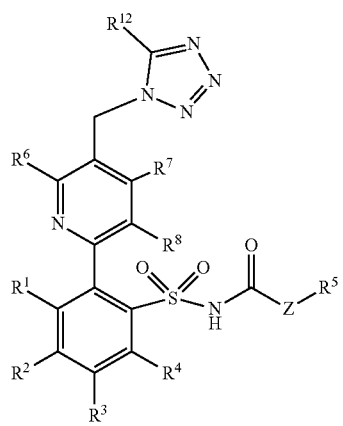
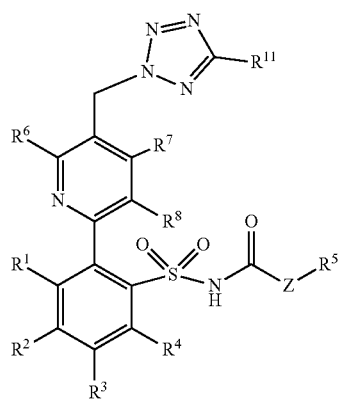
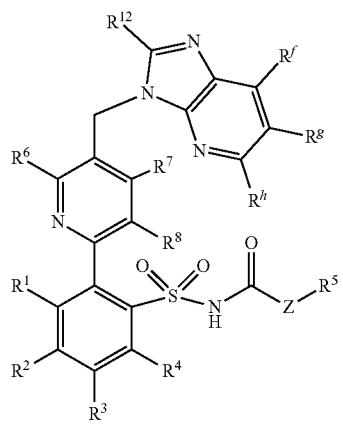

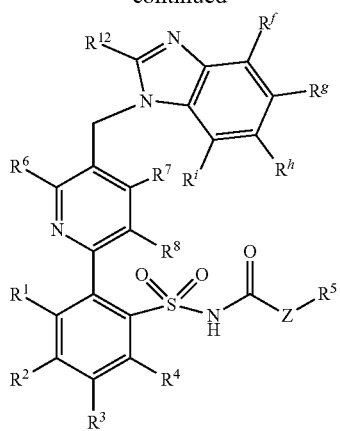
7
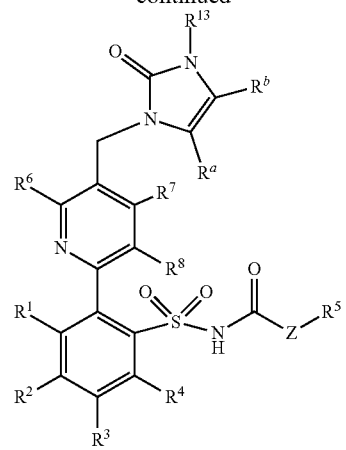
8
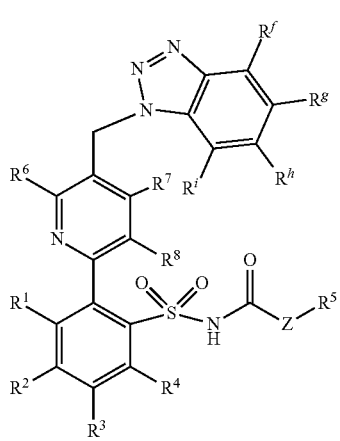
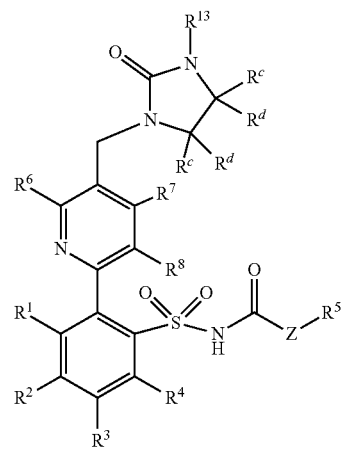
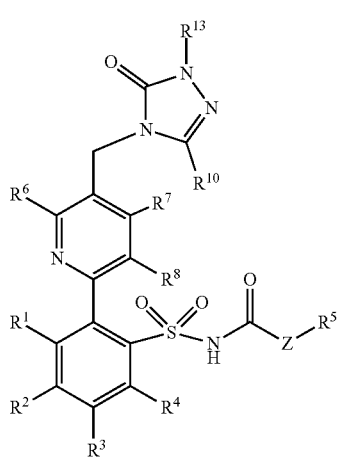
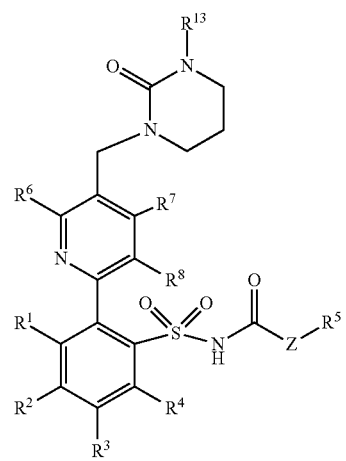

-continued

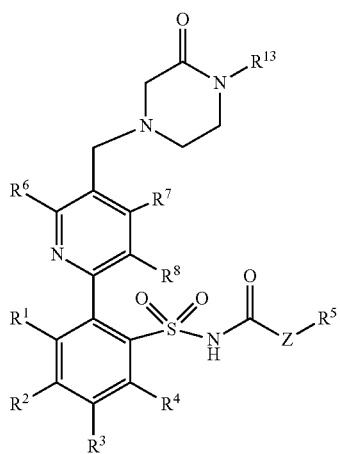

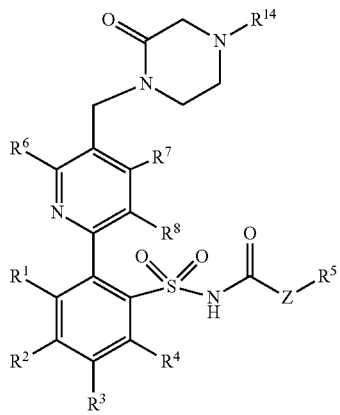

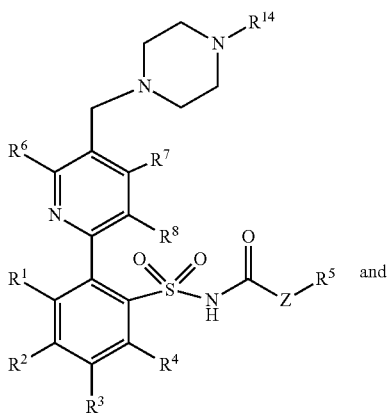 and

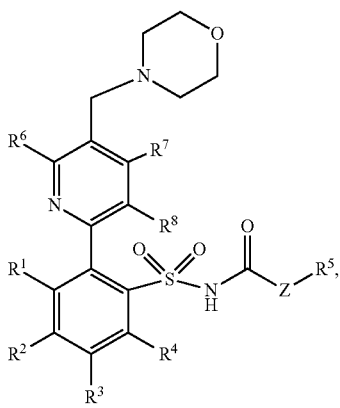

wherein:

$R^1$, $R^2$, $R^3$, $R^4$ $R^5$, $R^6$, $R^7$, $R^8$, $R^9$, $R^a$, $R^b$, $R^c$, $R^d$ and Z are defined as in general formula 1;

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy or $R^{10}$ and $R^{11}$, together with ring A to which they are attached, form a carbocyclic, heterocyclic, aryl or heteroaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, and aryloxyalkyl;

or a pharmaceutically acceptable salt thereof.

In various further embodiments, $R^2$ is trifluoromethoxy and/or Z is O or —N(H)—. In another embodiment, the compound has the general formula 4a or a pharmaceutically acceptable salt thereof:

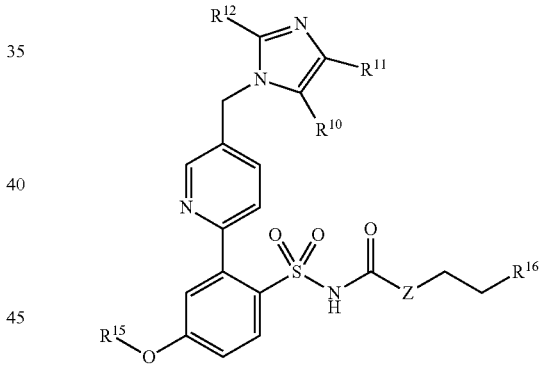

wherein:

Z is —O— or —N(H)—;

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy, or $R^{10}$ and $R^{11}$, together with ring A to which they are attached, form a carbocyclic, heterocyclic, aryl or heteroaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{15}$ is alkyl, aryl, heteroaryl, arylmethyl, heteroarylmethyl, trifluoromethyl or pentafluoroethyl; and $R^{16}$ is hydrogen, hydroxy, methoxy, alkoxy, alkyl, alkenyl, alkynyl, aryl, heteroaryl, amino, alkylamino, or dialkylamino.

In a further embodiment, the compound has the general formula 4a or a pharmaceutically acceptable salt thereof:

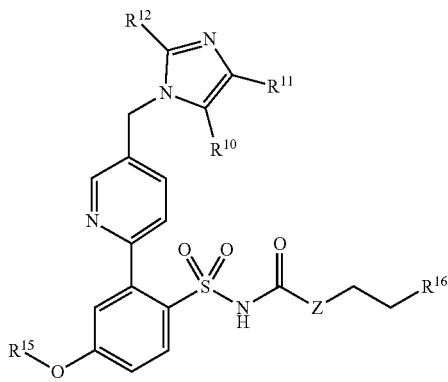

4a wherein:

Z is —O— or —N(H)—;

$R^{10}$, $R^{11}$ and $R^{12}$ are hydrogen;

$R^{15}$ is alkyl, aryl, heteroaryl, arylmethyl, heteroarylmethyl, trifluoromethyl or pentafluoroethyl; and $R^{16}$ is hydrogen, hydroxy, methoxy, alkoxy, alkyl, alkenyl, alkynyl, aryl, heteroaryl, amino, alkylamino, or dialkylamino.

In another embodiment, the compound has the general formula 4a or a pharmaceutically acceptable salt thereof:

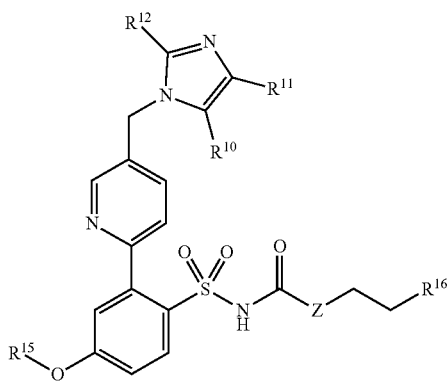

4a wherein:

Z is —O— or —N(H)—;

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{15}$ is trifluoromethyl and $R^{16}$ is ethyl

In a further embodiment, the compound has the formula 7 or a pharmaceutically acceptable salt thereof:

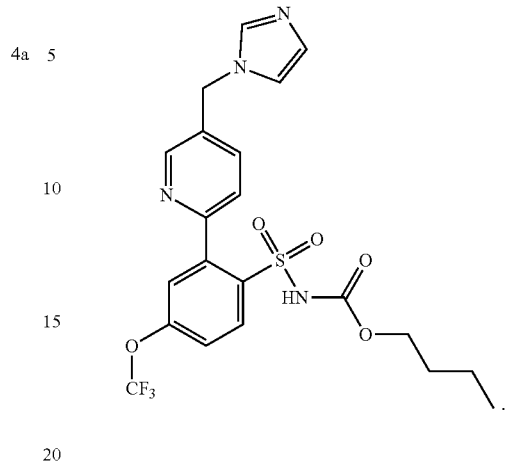

Compound 7

DESCRIPTION OF THE FIGURES

FIG. 1. 5 week-old wild-type (WT) and mdx mice were orally treated for 6 weeks with either vehicle (Veh) or 8 mg/kg of Compound 7 once or twice daily. (A) At necropsy, bone marrow was collected, cultured, and CFU-F counts were recorded which showing a significant increase in MSC with both once and twice daily treatment with Compound 7. (B) The percentage of CD45 negative cells triply positive for MSC markers Sca-1, CD29, & CD105 from the collected bone marrow was analyzed by flow cytometry. Relative to vehicle treated mdx mice, mdx mice treated with Compound 7 had significantly increased percentage of CD45 negative cells triply positive for Sca-1, CD29, & CD105 to levels comparable to vehicle treated wild-type mice. (C) The percentage of CD45 negative cells triply positive for MSC markers Sca-1, CD29, & CD105 from the peripheral blood was analyzed by flow cytometry showing a significant increase in circulating MSCs with twice a day oral treatment with Compound 7. *=P≤0.05, =P≤0.01, and *=P≤0.001 in comparison with vehicle control.

DETAILED DESCRIPTION

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

PCT Application PCT/US14/30071 provided novel non-peptidic compounds and compositions (including the synthesis thereof) capable of modulation the Mas receptor of the Renin-Angiotensin System (RAS) and/or capable of mimicking, in part or in entirety, the in vitro and in vivo activities of the endogenous Mas receptor ligand A (1-7).

The present invention describes the use of compounds and compositions for the increasing circulating mesenchymal stein cells (MSC), and thus use of the compounds for treating a variety of disorders that can benefit from increasing circulating MSC, including but not limited to myocardial infraction, graft versus host disease, diabetes, liver cirrhosis, spinal cord injury, osteoarthritis, Crohn's disease, multiple sclerosis, aplastic anemia, rheumatoid arthritis, Parkinson's disease, and brain injury.

In various embodiments, this invention provides methods for (a) treating a subject having a disorder selected from the group consisting of myocardial infraction, cardiovascular disease, graft versus host disease, diabetes, liver cirrhosis, liver disease, spinal cord injury, osteoarthritis, Crohn's disease, multiple sclerosis, aplastic anemia, rheumatoid arthritis, autoimmune disorders including alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barré syndrome, idiopathic thrombocytopenic purpura, myasthenia pemphigus/pemphigoid, pernicious anemia, polyarteritis nodosa, polymyositis, primary biliary, cirrhosis, psoriasis, scleroderma/systemic sclerosis, Sjögren's syndrome, some forms of thyroiditis, some forms of uveitis, vitiligo, granulomatosis with polyangiitis (Wegener's)), organ transplantation, organ rejection, Parkinson's disease, neurodegenerative disorders, amyotrophic lateral sclerosis, Alzheimer disease, brain injury, and inflammatory lung disease, comprising administering to subject in need thereof an amount effective to treat the disorder of a compound having the general formula 1 including salts thereof; or (b) increasing circulating mesenchymal stem cells (MSC) in a subject, comprising administering to a subject in need thereof an amount effective to increase circulating MSC in the subject of a compound having the general formula 1 or a pharmaceutically acceptable salt thereof:

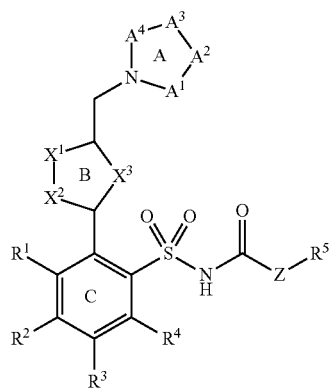

wherein:
ring A is a five-membered or six-membered heteroaryl or heterocyclyl ring containing either a combination of two non-adjacent nitrogen or oxygen atoms, or a combination of three or four nitrogen or oxygen atoms;
ring B is a five-membered or six-membered heteroaryl ring that contains at least one nitrogen atom;
$A^1$, $A^2$, $A^3$, $A^4$ are independently selected from a group consisting of =N—, —C(=O)—, —C($R^a$)=, =C($R^b$)—, —C($R^c$)($R^d$)—N($R^e$)—, —C($R^c$)($R^d$)—O—, and —[C($R^c$)($R^d$)]$_n$—, wherein n is 1 or 2;
$X^1$—$X^2$ is —($R^6$)C—N—, —N—C($R^6$)—, —N—N—, —N—O—, —O—N—, —N—S— or —S—N—;
$X^3$ is —($R^7$)C=C($R^8$)—, —O—, —S—, or —N($R^9$)—;
Z is —O—, —N(H)— or a bond to $R^5$;
$R^a$ and $R^b$ are independently selected from the group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido and carboxy, or $R^a$ and $R^b$ can also join to form a ring of up to 6 atoms;
$R^c$ and $R^d$ are independently selected from a group consisting of hydrogen, alkyl, aryl, or heteroaryl, provided that $R^c$ and $R^d$, together with the atoms to which they are attached, form a ring of up to 6 atoms;
$R^e$ is hydrogen, alkyl, aryl, heteroaryl, acyl, alkoxyacyl, aminoacyl, dialkylaminoacyl, or dialkylaminoacyl;
$R^1$, $R^3$, $R^4$, $R^6$, $R^7$, and $R^8$ are independently selected from a group consisting of hydrogen, alkyl, alkenyl, alkynyl, aryl, heteroaryl, aryl methyl, heteroarylmethyl, fluoro, chloro, bromo, iodo, cyano, hydroxy, amino, alkylamino, alkoxy, aryloxy, alkoxyalkyl and aryloxyalkyl;
$R^2$ is alkyl, alkenyl, alkynyl, aryl, heteroaryl, arylmethyl, heteroarylmethyl, alkoxy, trifluoromethoxy, perfluoroalkoxy, aryloxy, alkoxyalkyl, or aryloxyalkyl;
$R^5$ is alkyl, aryl, heteroaryl, hydroxyalkyl, carboxyalkyl, alkoxyalkyl, or aryloxyalkyl; and
$R^9$ is hydrogen, alkyl, aryl, heteroaryl, acyl, alkoxyacyl, aminoacyl, dialkylaminoacyl, or dialkylaminoacyl.

In exemplary embodiments, ring A includes but is not limited to a ring selected from a group consisting of:

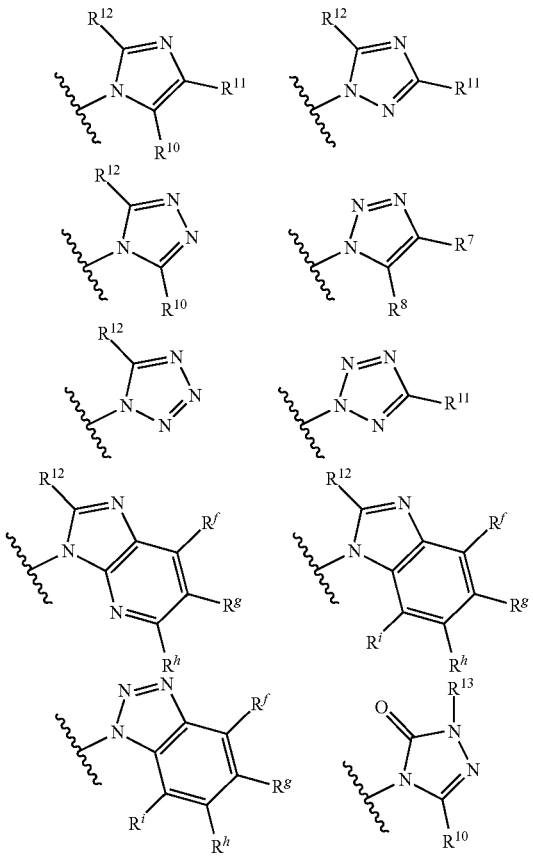

-continued

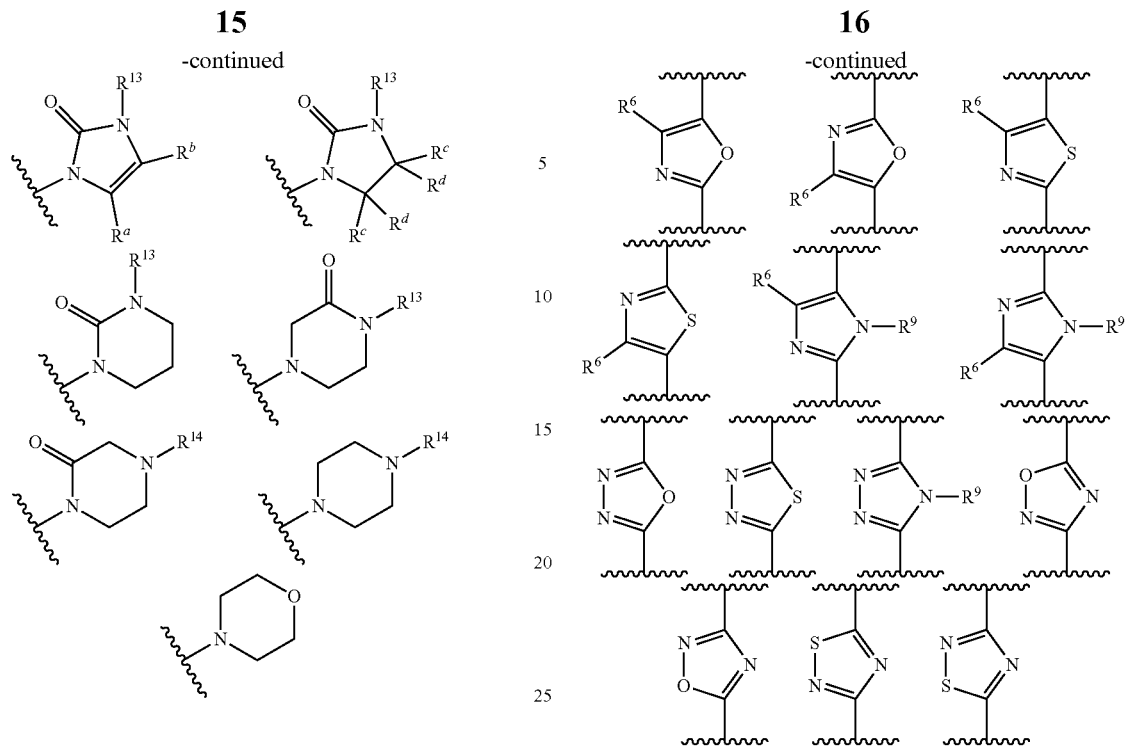

wherein:
- $R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;
- $R^{12}$ is hydrogen, alkyl, alkenyl, alkynyl, aryl, heteroaryl, halo, hydroxy, hydroxyalkyl, alkoxyalkyl, alkoxy, aryloxy, or acylamido;
- $R^{13}$ is hydrogen, alkyl, aryl or heteroaryl;
- $R^{14}$ is hydrogen, alkyl, aryl, heteroaryl, acyl, alkoxyacyl, aminoacyl, dialkylaminoacyl, or dialkylaminoacyl; and
- $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl.

In other exemplary embodiments, ring B includes but is not limited to a five- or six-membered heteroaryl ring selected from a group consisting of:

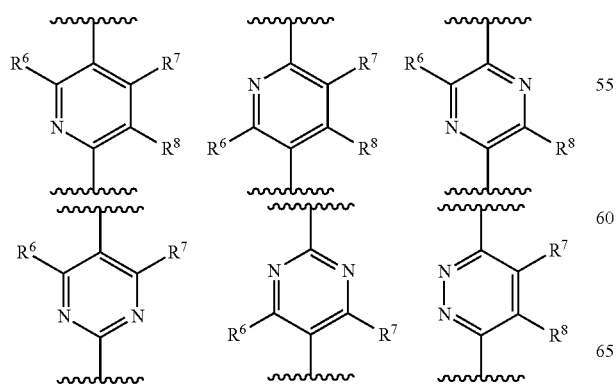

wherein groups $R^6$, $R^7$, $R^8$ and $R^9$ are defined as in general formula 1

In some exemplary embodiments, the compounds administered in connection with the methods and compositions provided herein have the general formula selected from a group consisting of:

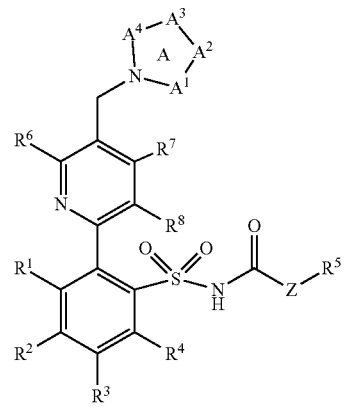

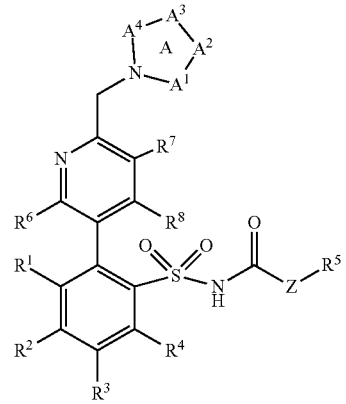

-continued
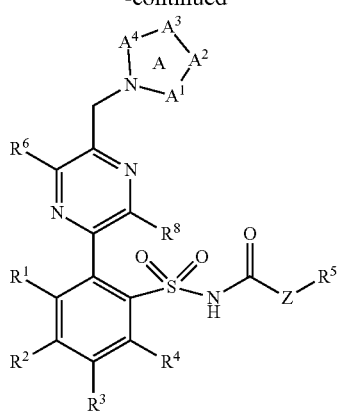
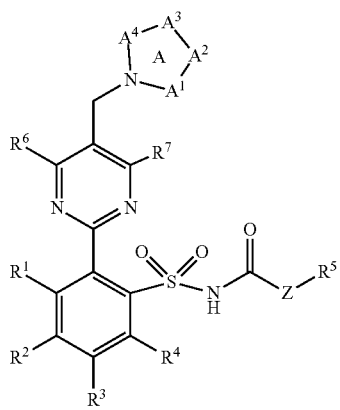
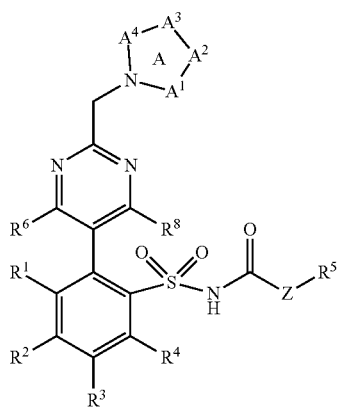
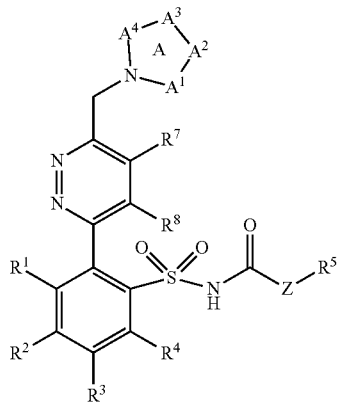
-continued
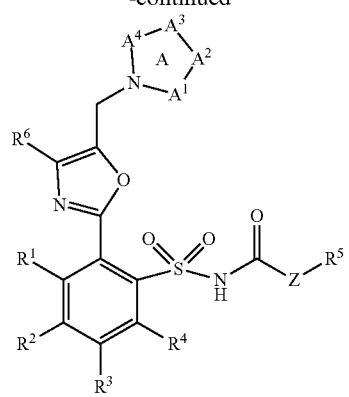
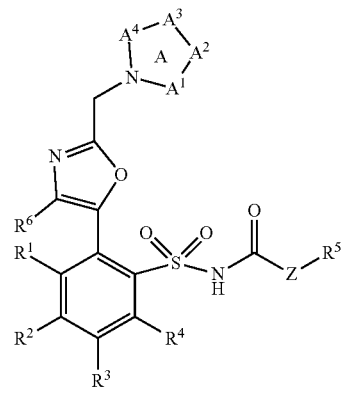
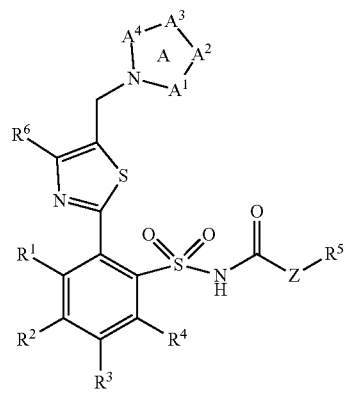
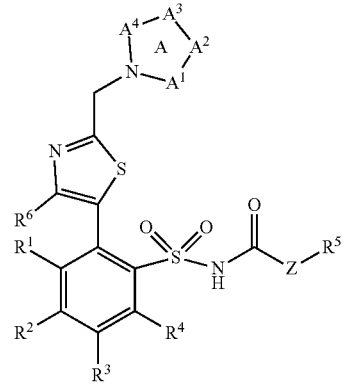

-continued
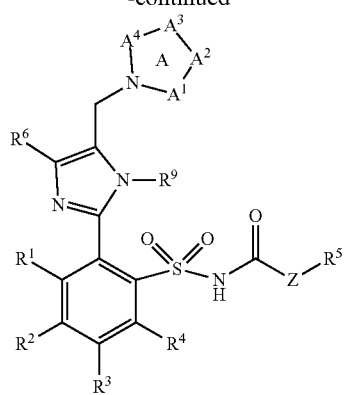
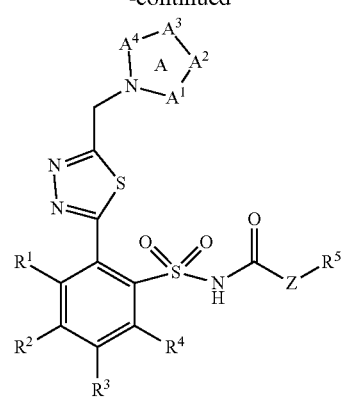
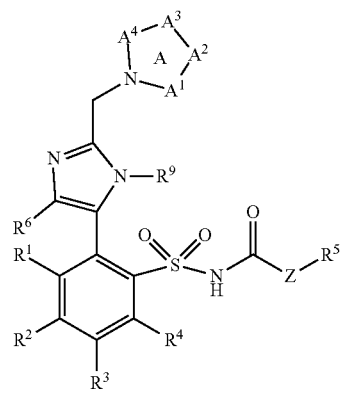
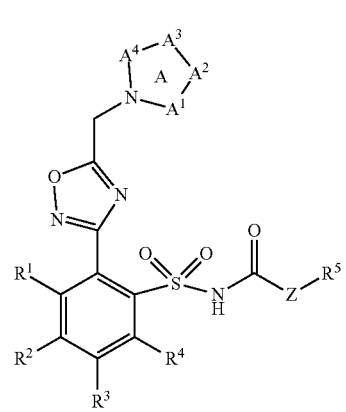
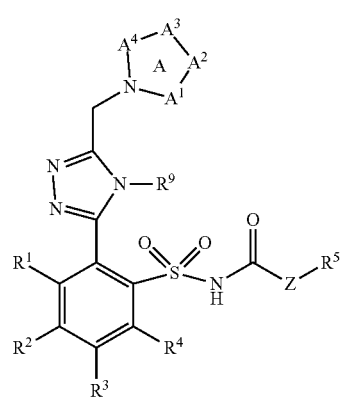
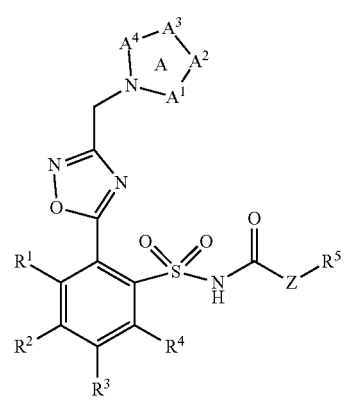
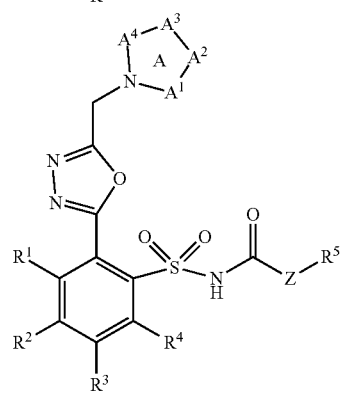
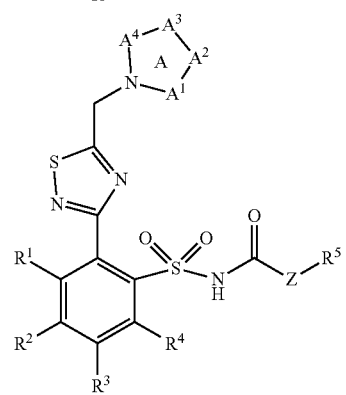

-continued
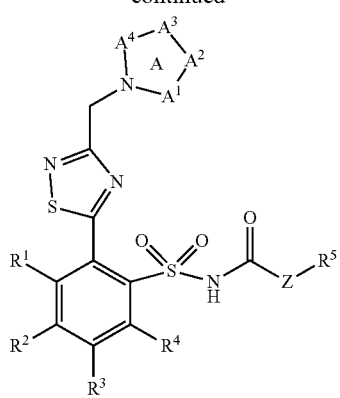
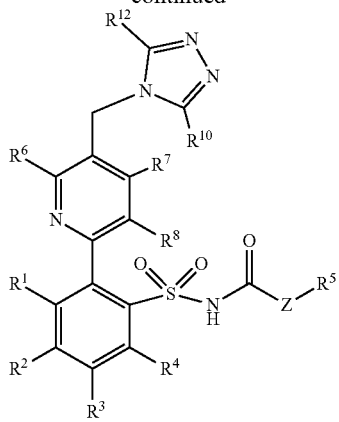
wherein groups R¹, R², R³, R⁴ R⁵, R⁶, R⁷, R⁸, R⁹, A¹, A², A³, A⁴ and Z are defined as in general formula 1.
In other exemplary embodiments, the compounds have the general formula selected from a group consisting of:
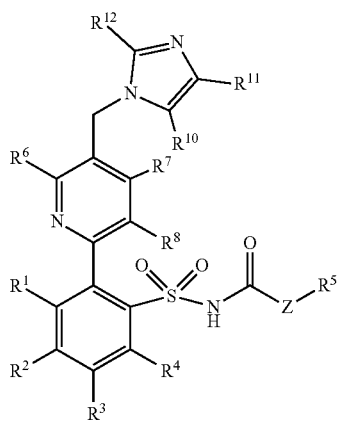
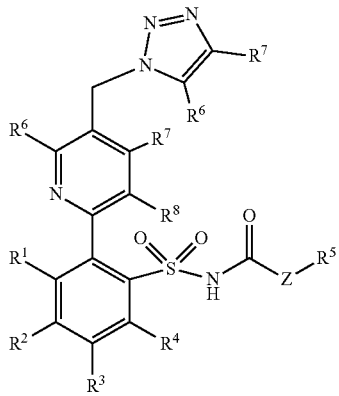
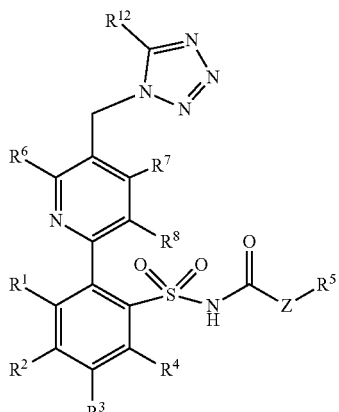
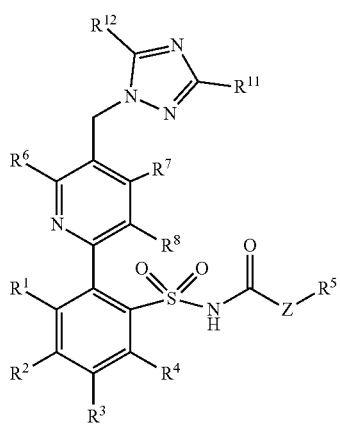
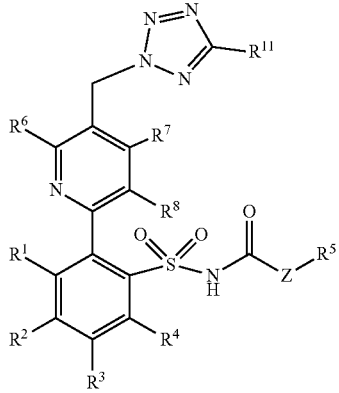

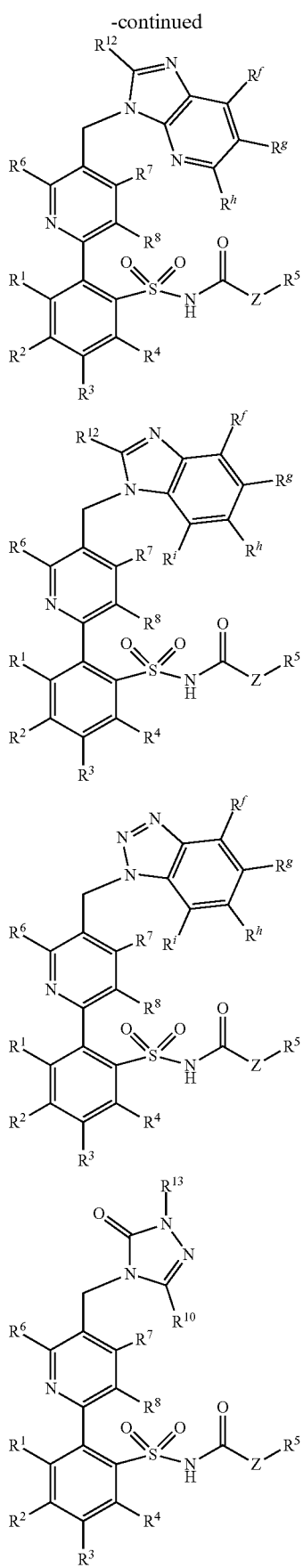
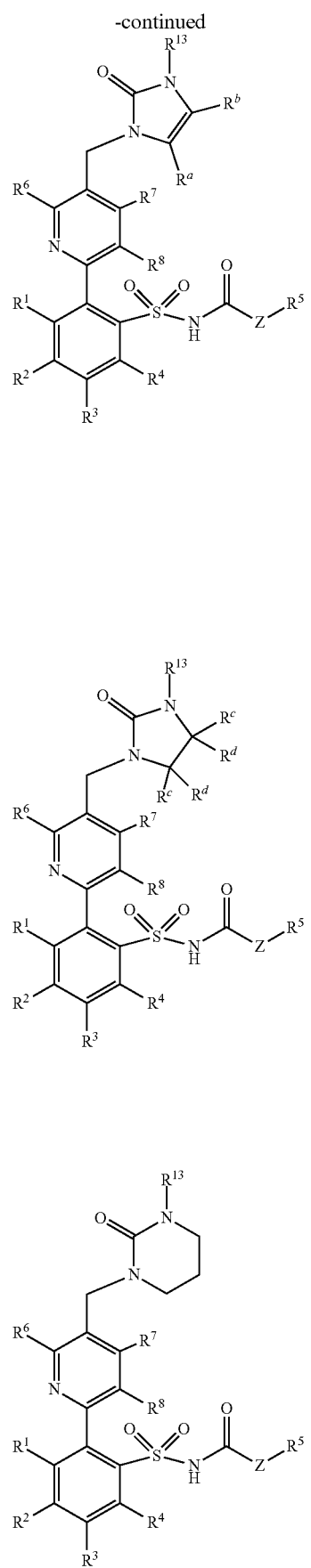

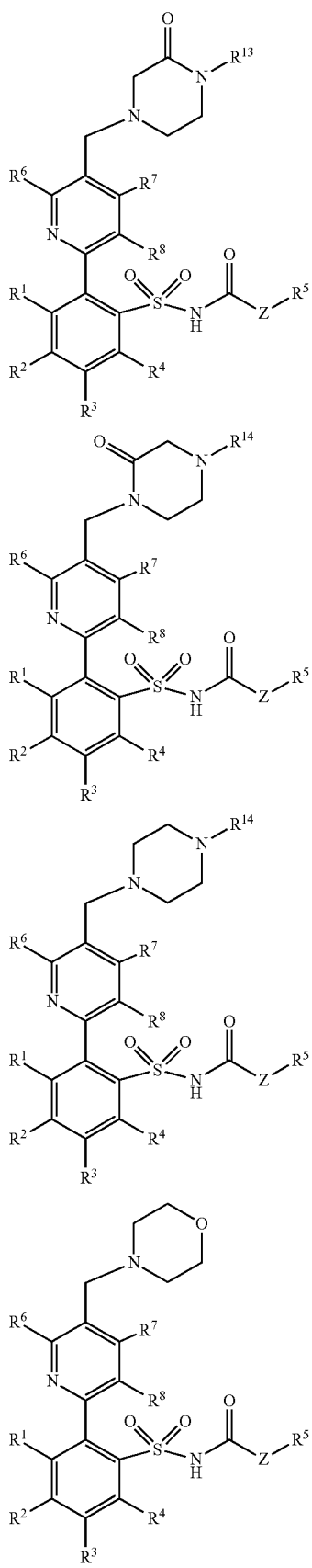

wherein:

R[1], R[2], R[3], R[4] R[5], R[6], R[7], R[8], R[9], R[a], R[b], R[c], R[d] and Z are defined as in general formula 1.

R[10] and R[11] are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that R[10] and R[11] can also be joined to form a carbocyclic, heterocyclic, aryl or hetoaryl ring;

R[12] is hydrogen, alkyl, alkenyl, alkynyl, aryl, heteroaryl, halo, hydroxy, hydroxyalkyl, alkoxyalkyl, alkoxy, aryloxy, or acylamido;

R[13] is hydrogen, alkyl, aryl or heteroaryl;

R[14] is hydrogen, alkyl, aryl, heteroaryl, acyl, alkoxyacyl, aminoacyl, dialkylaminoacyl, or dialkylaminoacyl; and R[f], R[g], R[h], and R[i], are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl.

In additional exemplary embodiments, the compounds administered in connection with the methods and compositions provided herein have the general formula selected from a group consisting of:

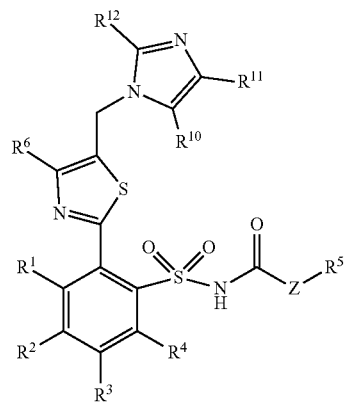

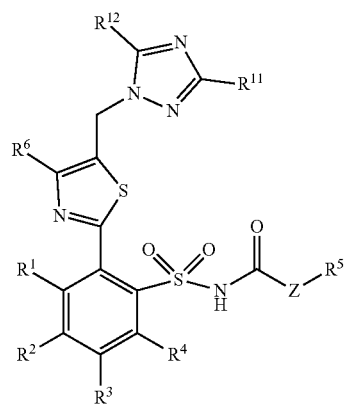

-continued
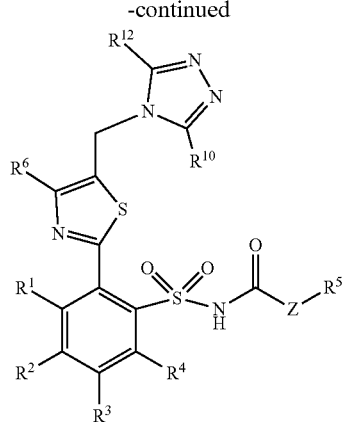
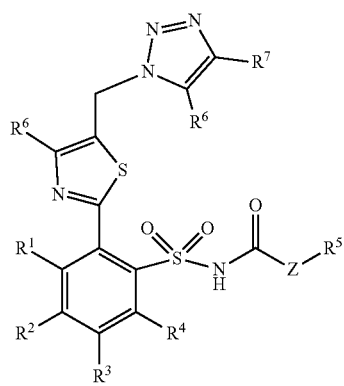
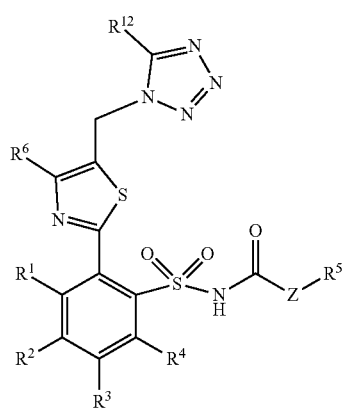
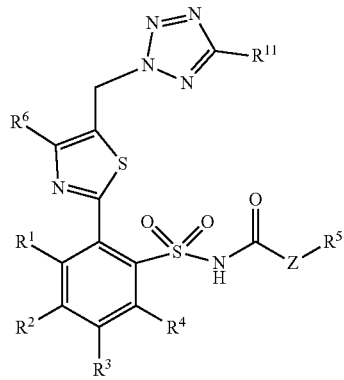
-continued
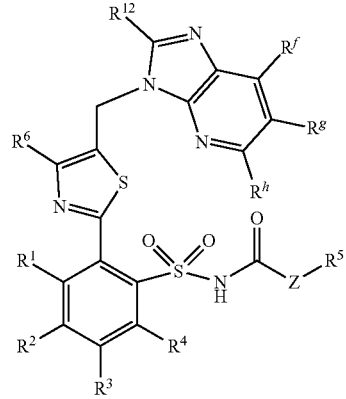
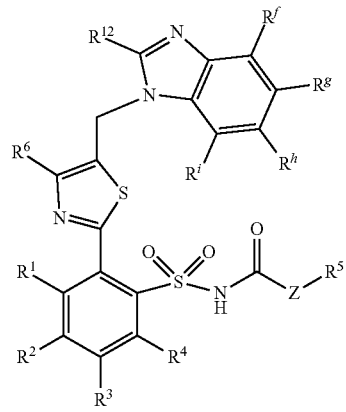
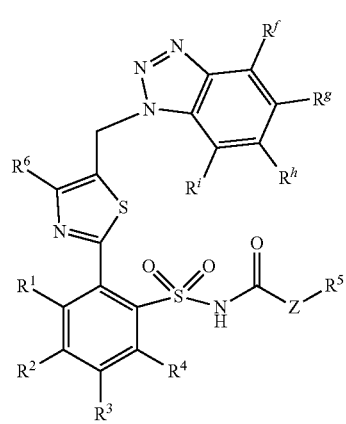
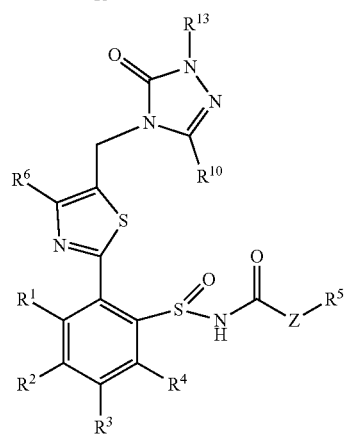

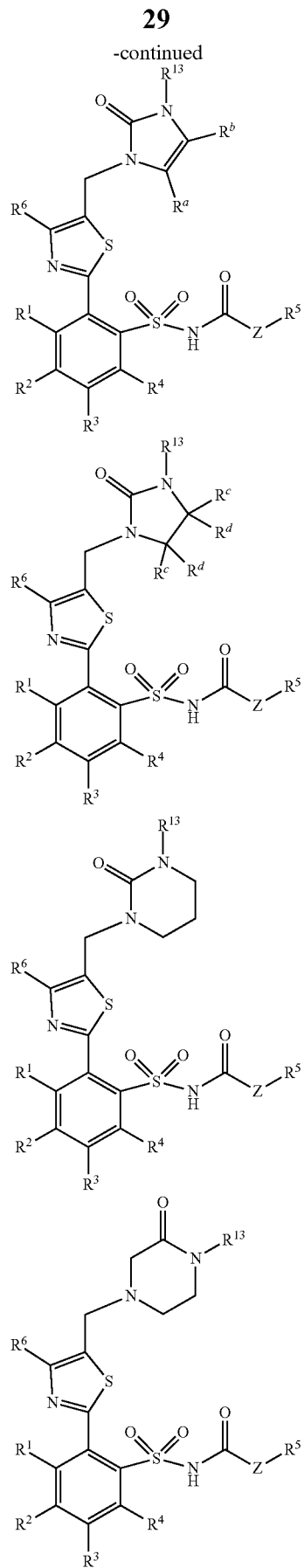
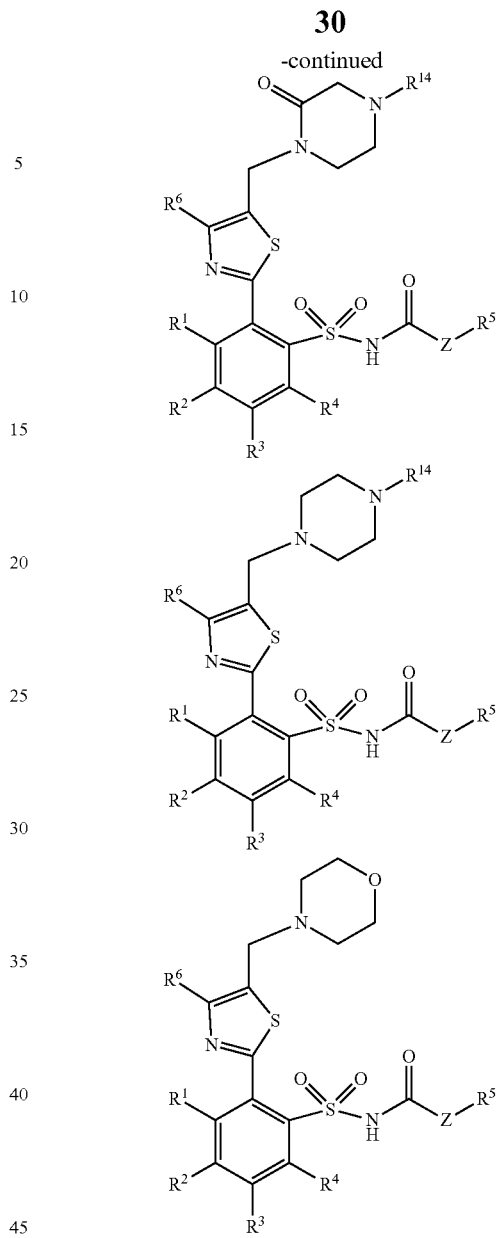

wherein:
$R^1, R^2, R^3, R^4 R^5, R^6, R^7, R^8, R^9, R^a, R^b, R^c, R^d$ and Z are defined as in general formula 1.
$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;
$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;
$R^{13}$ is hydrogen, alkyl, aryl or heteroaryl;
$R^{14}$ is hydrogen, alkyl, aryl, heteroaryl, acyl, alkoxyacyl, aminoacyl, dialkylaminoacyl, or dialkylaminoacyl; and
$R^f, R^g, R^h,$ and $R^i,$ are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl.

In some preferred embodiments, the compounds administered in connection with the methods provided herein have the general formula 2a,b or 3a,b:

2a
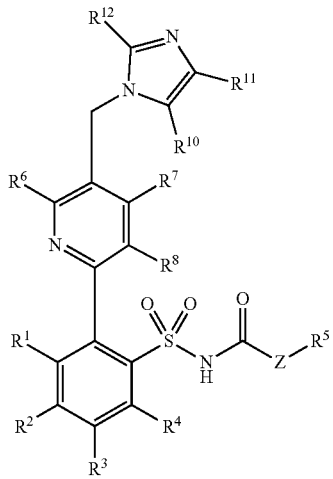

2b
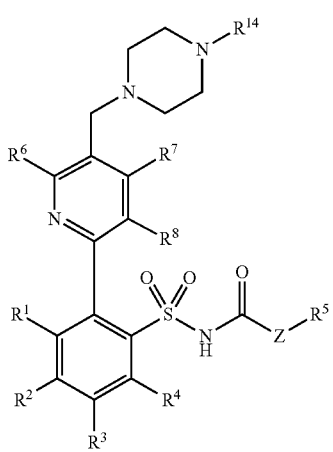

3a
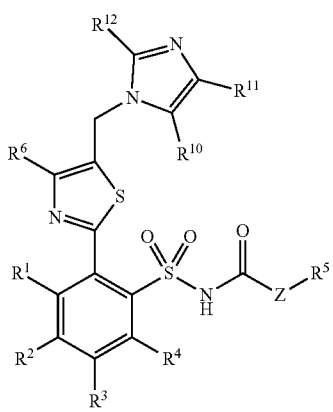

3b
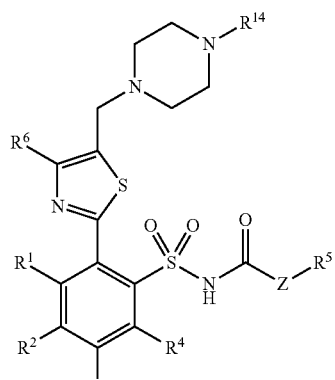

wherein:

$R^1$, $R^2$, $R^3$, $R^4$ $R^5$, $R^6$, $R^7$, $R^8$, $R^9$, $R^a$, $R^b$, $R^c$, $R^d$ and are defined as in general formula 1.

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{13}$ is hydrogen, alkyl, aryl or heteroaryl;

$R^{14}$ is hydrogen, alkyl, aryl, heteroaryl, acyl, alkoxyacyl, aminoacyl, dialkylaminoacyl, or dialkylaminoacyl; and $R^f$, $R^g$, $R^h$, and $R^i$, are independently selected from a group consisting of hydrogen, alkyl, alkenyl, alkynyl, aryl, heteroaryl, arylmethyl, heteroarylmethyl, fluoro, chloro, bromo, iodo, hydroxy, amino, alkylamino, alkoxy, aryloxy, alkoxyalkyl, or aryloxyalkyl.

In further preferred embodiments the compounds administered in connection with the methods and compositions provided herein having the general formula 4a,b, 5a,b or 6a,b:

4a
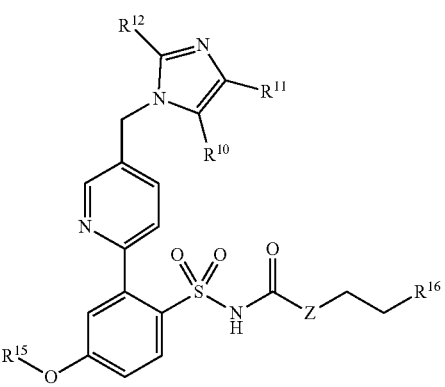

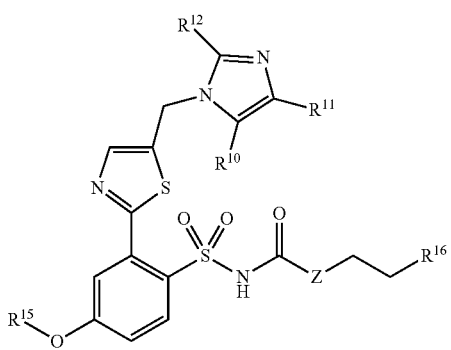

4b

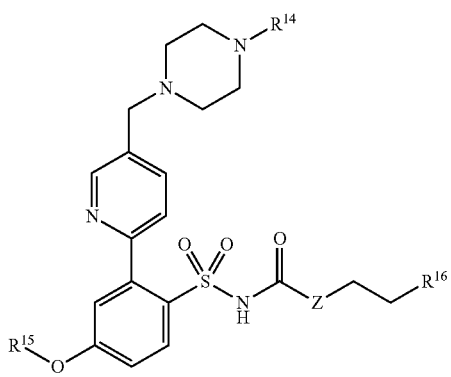

5a

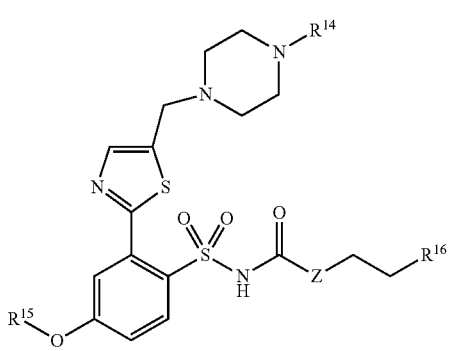

5b

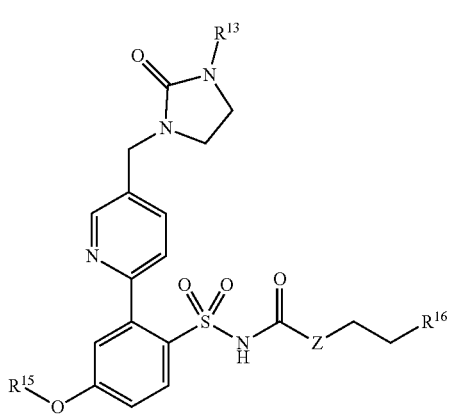

6a

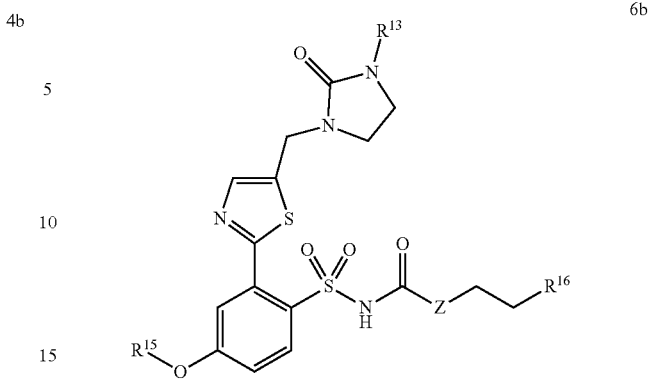

6b wherein:
$R^1$, $R^2$, $R^3$, $R^4$ $R^5$, $R^6$, $R^7$, $R^8$, $R^9$, $R^a$, $R^b$, $R^c$, $R^d$ and Z are defined as in general formula 1.

$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{14}$ is hydrogen, alkyl, aryl, heteroaryl, acyl, alkoxyacyl, aminoacyl, dialkylaminoacyl, or dialkylaminoacyl; and $R^{15}$ is alkyl, aryl, heteroaryl, arylmethyl, heteroarylmethyl, trifluoromethyl or pentafluoroethyl; and $R^{10}$ is hydrogen, hydroxy, methoxy, alkoxy, alkyl, alkenyl, alkynyl, aryl, heteroaryl, amino, alkylamino, or dialkylamino.

In some exemplary embodiments, the $R^{10}$, $R^{11}$ and $R^{12}$ are hydrogen, and $R^{14}$ is methyl.

In other exemplary embodiments, $R^{15}$ is trifluoromethyl and $R^{16}$ is ethyl.

Preferred embodiments of the compounds administered in connection with the methods and compositions provided herein have the general formula 4a:

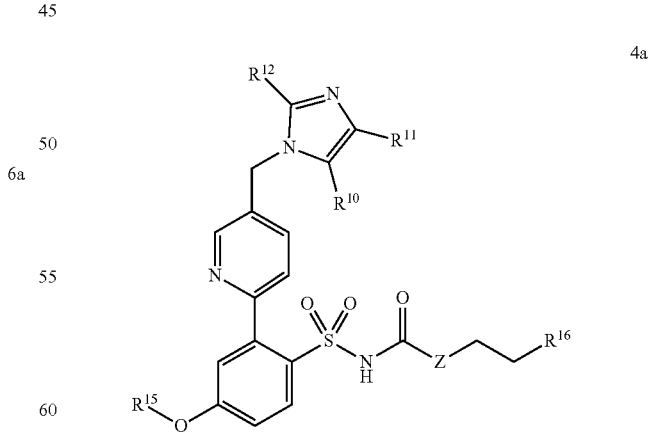

4a wherein:
Z is O or —N(H)—;
$R^{10}$ and $R^{11}$ are independently selected from a group consisting of hydrogen, alkyl, alkenyl, alkynyl, aryl, heteroaryl, halo, hydroxy, hydroxyalkyl, alkoxyalkyl, alkoxy, aryloxy, formyl, acyl, acylamido or carboxy, provided that $R^{10}$ and $R^{11}$ can also be joined to form a carbocyclic, heterocyclic, aryl or hetoaryl ring;

$R^{12}$ is hydrogen, alkyl, alkenyl, alkynyl, aryl, heteroaryl, halo, hydroxy, hydroxyalkyl, alkoxyalkyl, alkoxy, aryloxy, or acylamido;

$R^{15}$ is alkyl, aryl, heteroaryl, arylmethyl, heteroarylmethyl, trifluoromethyl or pentafluoroethyl; and $R^{16}$ is hydrogen, hydroxy, methoxy, alkoxy, alkyl, alkenyl, alkynyl, aryl, heteroaryl, amino, alkylamino, or dialkylamino.

In some exemplary embodiments, the $R^{10}$, $R^{11}$ and $R^{12}$ are hydrogen.

In exemplary embodiments, $R^{15}$ is trifluoromethyl and $R^{16}$ is ethyl.

Exemplary embodiments of compounds administered in connection with the methods provided herein are provided by compounds 7, 8, 9, 10, and 11:

A representative exemplary embodiment of the provided methods disclosed herein comprises the administration of Compound 7:

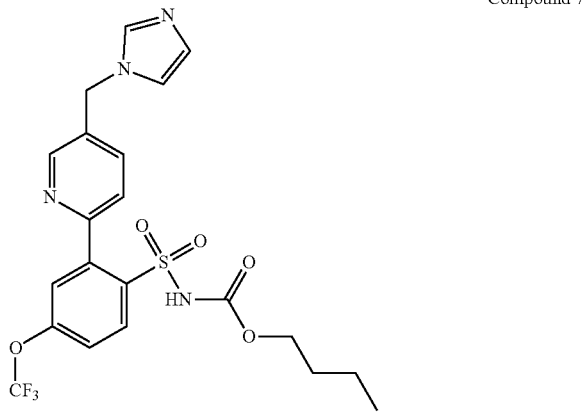

Compound 7

The invention further provides pharmaceutical compositions for the methods of the invention, comprising a compound provided in PCT Application PCT/US14/30071 or a pharmaceutically acceptable salt, and a pharmaceutically acceptable carrier as described in PCT Application PCT/US14/30071. The provided methods and compositions are employed in any suitable administrative form, including but not limited to oral, parenteral, or topical administration.

The invention is further described in the attached examples, which are illustrative only, and which are not intended to limit the scope of the invention described in the claims.

Definitions

Unless defined otherwise, all technical and scientific terms used herein have the same meaning as is commonly understood by one of ordinary skill in the art. In the event that there is a plurality of definitions for a term herein, those in this section will control unless stated otherwise.

As used herein, the terms "treatment", "treating", and the like, refer to obtaining a desired pharmacologic and/or physiologic effect. The effect may be therapeutic in terms of a partial or complete cure for a disease and/or adverse symptoms attributable to the disease. "Treatment", as used herein, covers any treatment of the recited disorders, particularly in a human, and includes: (a) limiting development of symptoms or flares from occurring in a subject having the disorder; (b) limiting worsening of symptoms or flares in a subject having the disorder; (c) inhibiting the disorder, i.e., arresting development of the disorder; (d) relieving the disorder, i.e., causing regression of the disorder.

Increasing circulating mesenchymal stem cells (MSC) as used herein may mean any increase over control (such as a subject not treated with the compounds of the invention), as any such increase will provide a therapeutic benefit to the subject. In various non-limiting embodiments, the methods increase circulating MSC in the subject at least 5% compared to control; in other embodiments, at least 10%, 15%, 20%, 25%, or more compared to control.

The terms "individual," "subject," and "patient," used interchangeably herein, refer to a mammal, including, but not limited to, murines, simians, humans, mammalian farm animals, mammalian sport animals, and mammalian pets. Preferably, the subject herein is human, such as a human female.

As used herein, the nomenclature alkyl, alkoxy, carbonyl, etc. is used as is generally understood by those of skill in the chemical art. As used in this specification, alkyl groups can include straight-chained, branched and cyclic alkyl radicals containing up to about 20 carbons, or 1 to 16 carbons, and are straight or branched. Exemplary alkyl groups herein include, but are not limited to, methyl, ethyl, propyl, isopropyl, isobutyl, n-butyl, sec-butyl, tert-butyl, isopentyl, neopentyl, tert-pentyl and isohexyl. As used herein, lower alkyl refer to carbon chains having from about 1 or about 2 carbons up to about 6 carbons. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, "cycloalkyl" refers to a mono- or multicyclic ring system, in certain embodiments of 3 to 10 carbon atoms, in other embodiments of 3 to 6 carbon atoms. The ring systems of the cycloalkyl group may be composed of one ring or two or more rings which may be joined together in a fused, bridged or spiro-connected fashion.

As used herein, "aryl" refers to aromatic monocyclic or multicyclic groups containing from 3 to 16 carbon atoms. As used in this specification, aryl groups are aryl radicals, which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from a group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, phosphonate, phosphonamido, and sulfonyl, and further provided that the ring may also contain one or more fused rings, including carbocyclic, heterocyclic, aryl or heteroaryl rings.

The term "alkenyl" refers to a branched or unbranched hydrocarbon having at least one carbon-carbon double bond.

The term "alkynyl" refers to a branched or unbranched hydrocarbon having at least one carbon-carbon triple bond.

The term "carboxy" refers to a —CO$_2$H group.

The term "hydroxy" refers to an —OH group.

The term "alkoxy" refers to a group of the formula R—O— where R is an "alkyl" as defined herein.

The term "carbocycle" refers to a non-aromatic stable 3- to 8-membered carbon ring which may be saturated, mono-unsaturated or poly-unsaturated.

The term "amino" includes primary, secondary or tertiary amino groups.

The term "cyano" refers to the group —CN.

As used herein, alkenyl and alkynyl carbon chains, if not specified, contain from 2 to 20 carbons, or 2 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds.

As used herein, "heteroaryl" refers to a monocyclic or multicyclic aromatic ring system, in certain embodiments, of about 4 to about 15 members where one or more, in one embodiment 1 to 4, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, triazolyl, tetrazolyl, thienyl, pyridyl, pyrrolyl, N-methylpyrrolyl, quinolinyl and isoquinolinyl.

As used herein, "heterocyclyl" refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, "aralkyl" refers to an alkyl group in which one of the hydrogen atoms of the alkyl is replaced by an aryl group.

As used herein, "halo", "halogen" or "halide" refers to F, Cl, Br or I.

As used herein, "haloalkyl" refers to an alkyl group in which one or more of the hydrogen atoms are replaced by halogen. Such groups include, but are not limited to, chloromethyl and trifluoromethyl.

As used herein, "aryloxy" refers to RO—, in which R is aryl, including lower aryl, such as phenyl.

As used herein, "acyl" refers to a —COR group, including for example alkylcarbonyl, cycloalkylcarbonyl, arylcarbonyl, or heteroarylcarbonyls, all of which may be optionally substituted.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944).

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

EXAMPLES

Summary: We show herein that small molecule Mas receptor agonists increase circulating mesenchymal stem cells (MSCs). We have shown decreased bone marrow MSCs of two chronic inflammatory diseases, diabetes and Duchenne muscular dystrophy (DMD), relative to their wild-type, non-disease control. Disclosed herein is the discovery that Mas agonists induce an increase in the therapeutically valuable circulating MSCs, as measured by flow cytometry in the peripheral blood.

DMD is one of the most common and devastating genetic diseases of childhood caused by mutations in the DMD gene resulting in the loss of functional dystrophin protein. In unaffected individuals, dystrophin serves a stabilizing role in muscle cells including cardiomyocytes. Due to dystrophin deficiency, the muscle cells in DMD patients are predisposed to contraction-induced damage. Over time, successive cycles of injury and repair lead to a state of chronic inflammation, oxidative stress, and fibrosis which reduces the regenerative capacity of the muscle and drains satellite cell pools.

In the mdx mouse model of DMD, 5 week-old wild-type (C57BL/10SnJ) and mdx (C57BL/10ScSn-Dmd$^{mdx}$/J) mice were treated for 6 weeks and necropsied. These mice were broken into 4 orally dosed groups: a wild-type group (n=5) dosed twice daily with vehicle, an mdx group (n=8) dosed twice daily with vehicle, an mdx group (n=8) dosed once daily with 8 mg/kg of Compound 7, and an mdx group (n=8) dosed twice daily with 8 mg/kg of Compound 7. The vehicle was a 1% β-cyclodextrin in ~pH 3 citrate buffer and the treatment 1% β-cyclodextrin in ~pH 3 citrate buffer with Compound 7. At necropsy, the femur bone marrow was isolated and peripheral blood was harvested. The bone marrow was cultured in Mesencult™ MSC Basal Medium (mouse) supplemented with Mesencult™ MSC Stimulatory Supplement (Stemcell Technologies). CFU-F colonies of ≥50 cells were counted after 8 days in culture. Daily oral treatment with Compound 7 significantly increased bone marrow MSCs with the twice daily dosing restoring levels comparable to the non-dystrophic controls (FIG. 1A).

Assessment of MSCs by flow cytometry focused on non-hematopoietic cells (CD45 negative) that were positive for mouse MSC markers Sca-1 (stem cell antigen-1), CD29 (integrin $\beta_1$), and CD105 (endoglin). Analysis of the bone marrow showed a similar significant increase in the percentage cells triply positive for MSC markers (Sca-1, CD29, & CD105) in non-hematopoietic cells (CD45 negative) in mdx mice treated with Compound 7 over mdx mice treated with vehicle. In fact, Compound 7 treatment restored the percentage of these triply positive cells to levels comparable to non-dystrophic controls (FIG. 1B). However, unexpectedly, in the peripheral blood, twice daily oral treatment with Compound 7 resulted in significantly higher percentages of non-hematopoietic cells triply positive for MSC markers than both mdx and wild-type mice treated with vehicle, illustrating the ability of this representative small molecule Mas agonist at increasing circulating MSCs (FIG. 1C).

Method

At necropsy, the femurs were also collected in a 1.5 mL microcentrifuge tube containing ~800 µL of sterile Dulbecco's phosphate-buffered saline (DPBS) with 2% fetal bovine serum (FBS) and 2× Penicillin (Pen) and 2× Streptomycin (Strep) (DPBS/2% FBS/2× Pen/Strep) and stored on ice. In a biosafety cabinet, both femurs from each mouse were cleaned of muscle with gauze, cut at both ends, and flushed into a 5 mL culture tubes with ~3 mL of sterile DPBS/2% FBS/2× Pen/Strep in a 3 mL syringe fitted with a 25G needle. The tubes were spun at 1,000 RPM for 10 minutes at 4° C., resulting in a pellet. The supernatant was discarded and the marrow was resuspended with 1 mL of sterile DPBS with 2% FBS and 2× Pen/Strep. The cell solutions were counted with a Z1 Coulter Counter (Beckman Coulter) and resuspended at 5*10$^6$ cells/mL. Two mL of Mesencult™ MSC Basal Medium (mouse) (Stemcell Technologies) supplemented with Mesencult™ MSC Stimulatory Supplement (mouse) (Stemcell Technologies) were added to each well of a 24 well plate along with 100 µL of cells from each respective sample. The plates were incubated for 8 days at 37° C. and 5% $CO_2$. On day 8, the colonies of ≥50 were counted by light microscopy.

During the necropsy, the blood was collected by cardiac puncture with a 1 mL syringe fitted with a 22G needle, transferred into 2 ml K3E K3EDTA VACUETTE® tubes, and stored on ice. The tubes were then spun at 1,500 RPM for 15 min at 4° C. The plasma (top layer) was collected. The remaining pellet was resuspended with 500 µL of sterile DPBS/2% FBS/2× Pen/Strep, layered over 1 mL of Ficol-Paque™ PLUS (GE Healthcare) in a 5 mL culture tube, and centrifuged at 1,200 RPM for 30 min at 4° C. with no brake. The resulting buffy coat was then collected with a 200 µL pipette, placed in a 5 mL culture tube, and washed (2 mL of sterile DPBS/2% FBS/2× Pen/Strep, centrifuged at 1,200 RPM for 5 min at 4° C. and supernatant decanted). The pellet was resuspended in 0.5 mL of sterile DPBS/2% FBS/2× Pen/Strep. The cell solutions were counted with a Z1 Coulter Counter (Beckman Coulter) and resuspended at 5*10$^6$ cells/mL. 400 µL of the 5*10$^6$ cells/mL solution was added to a 5 mL culture tube, the tube was centrifuge at 1,200 RPM at 4° C. for 15 minutes, and the supernatant removed. The pellet was re-suspend in 50 µL of blocking buffer (1 part Fc block and 10 parts DPBS/2% FBS) and incubated at 4° C. for 15 minutes. To this solution was added 50 µL of antibody cocktail (5 µL of CD105-FITC (clone: MJ7/18), CD45-PerCP (clone: 30F11), CD29-PE (clone: HMβ1-1), and Anti-Sca-1-APC (clone: D7), and 30 µL of DPBS/2% FBS) which was incubated at 4° C. for 30 minutes. After this time, 3 mL of cold PBS was added and the tube was centrifuge at 1,200 RPM at 4° C. for 15 min. The supernatant was then removed, re-suspend in 500 µL 10% neutral buffered formalin, covered with aluminum foil, and stored at 4° C. until analyzed. Samples were then read on a LSR II flow cytometer (BD Biosciences, San Jose, Calif.). Data was analyzed using FlowJo™ V 10.0.7r2.

REFERENCES

Blake D J, Weir A, Newey S E, Davies K E. Function and genetics of dystrophin and dystrophin-related proteins in muscle. Physiol Rev. 2002 April; 82(2):291-329.

Bruder S P, Jaiswal N, Haynesworth S E. Growth kinetics, self-renewal, and the osteogenic potential of purified human mesenchymal stein cells during extensive subcultivation and following cryopreservation. J Cell Biochem. 1997; 64:278-294.

Dennis J E, Merriam A, Awadallah A, Yoo J U, Johnstone B, Caplan A I. A quadripotential mesenchymal progenitor cell isolated from the marrow of an adult mouse. J Bone Miner Res. 1999; 14:700-709.

Ferrari G, Cusella-De Angelis G, Coletta M, Paolucci E, Stornaiuolo A, Cossu G, Mavilio F. Muscle regeneration by bone marrow-derived myogenic progenitors. Science. 1998; 279:1528-1530.

Fischer U M, Harting M T, Jimenez F, Monzon-Posadas W O, Xue H, Savitz S I, Laine G A, Cox C S Jr. Pulmonary passage is a major obstacle for intravenous stem cell delivery: the pulmonary first-pass effect. Stem Cells Dev. 2009 June; 18(5):683-92.

Gao F, Chiu S M, Motan D A, Zhang Z, Chen L, Ji H L, Tse H F, Fu Q L, Lian Q. Mesenchymal stem cells and immunomodulation: current status and future prospects. Cell Death Dis. 2016 Jan. 21; 7: e2062.

Hoffman E P, Brown R H Jr, Kunkel L M. Dystrophin: the protein product of the Duchenne muscular dystrophy locus. Cell. 1987 Dec. 24; 51(6):919-28.

Houlihan D D, Mabuchi Y, Morikawa S, Niibe K, Araki D, Suzuki S, Okano H, Matsuzaki Y. Isolation of mouse mesenchymal stem cells on the basis of expression of Sca-1 and PDGFR-α. Nat Protoc. 2012 December; 7(12):2103-11.

Iyer S S, Rojas M. Anti-inflammatory effects of mesenchymal stem cells: novel concept for future therapies. Expert Opin Biol Ther. 2008 May; 8(5):569-81.

Klingler W, Jurkat-Rott K, Lehmann-Horn F, Schleip R. The role of fibrosis in Duchenne muscular dystrophy. Acta Myol. 2012 December; 31(3):184-95.

Liu Y, Yan X, Sun Z, Chen B, Han Q, Li J, Zhao R C. Flk-1+ adipose-derived mesenchymal stem cells differentiate into skeletal muscle satellite cells and ameliorate muscular dystrophy in mdx mice. Stem Cells Dev. 2007 October; 16(5):695-706.

Lynch G S. Role of contraction-induced injury in the mechanisms of muscle damage in muscular dystrophy. Clin Exp Pharmacol Physiol. 2004 August; 31(8):557-61.

Markert C D, Atala A, Cann J K, Christ G, Furth M, Ambrosio F, Childers M K. Mesenchymal stem cells: emerging therapy for Duchenne muscular dystrophy. PM R. 2009 June; 1(6):547-59.

Petrof B J, Shrager J B, Stedman H H, Kelly A M, Sweeney H L. Dystrophin protects the sarcolemma from stresses developed during muscle contraction. Proc Natl Acad Sci USA. 1993 Apr. 15; 90(8):3710-4.

Wei X, Yang X, Han Z P, Qu F F, Shao L, Shi Y F. Mesenchymal stem cells: a new trend for cell therapy. Acta Pharmacol Sin. 2013 June; 34(6):747-54.

Young R G, Butler D L, Weber W, Caplan A I, Gordon S L, Fink D J. Use of mesenchymal stem cells in a collagen matrix for Achilles tendon repair. J Orthop Res. 1998; 16:406-413.

What is claimed is:

1. A method for increasing circulating mesenchymal stem cells (MSC) in a subject, comprising administering to a subject in need thereof an amount effective to increase circulating MSC to a therapeutically valuable level in the subject of a compound of formula 7, 8, 9, 10, or 11 or a pharmaceutically acceptable salt thereof:

Compound 7

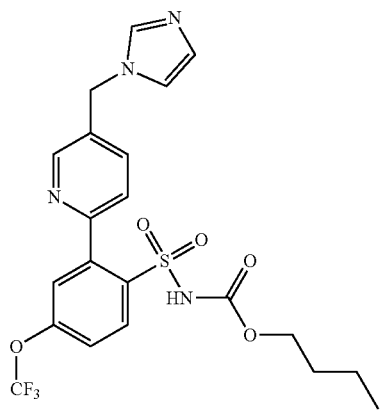

Compound 8

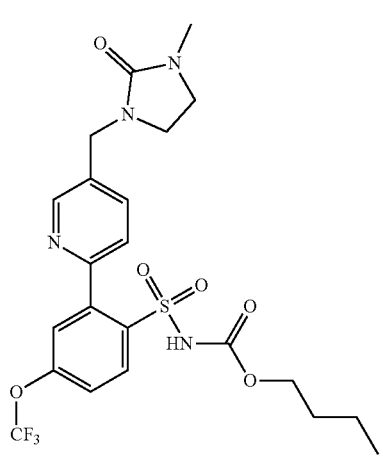

Compound 9

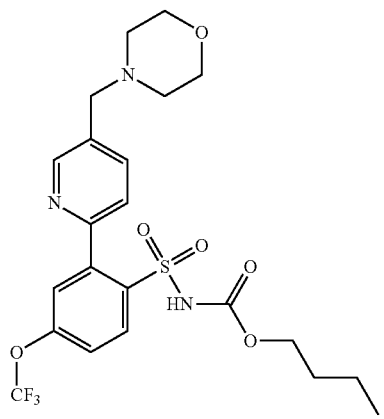

Compound 10

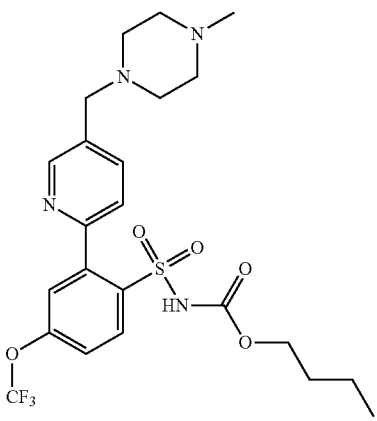

Compound 11

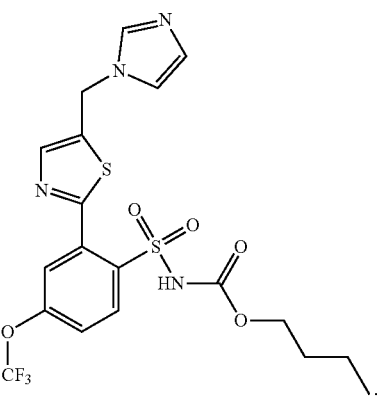

wherein the subject has a disorder selected from the group consisting of osteoarthritis, aplastic anemia, autoimmune hemolytic anemia, dermatomyositis, Graves' disease, idiopathic thrombocytopenic purpura, pemphigus/pemphigoid, polyarteritis nodosa, psoriasis, Sjögren's syndrome, granulomatosis with polyangiitis, and organ rejection, and wherein the method serves to treat the disorder.

2. The method of claim 1, wherein the compound has the formula 7, or a pharmaceutically acceptable salt thereof:

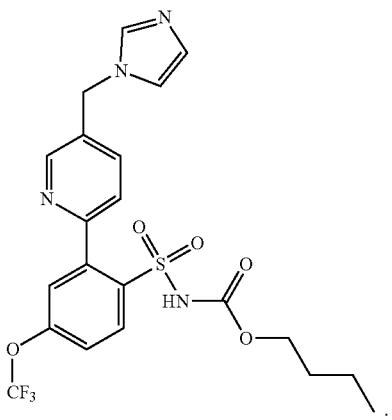

Compound 7

3. The method of claim 1, wherein the provided compound or pharmaceutically acceptable salt thereof is provided as a composition comprising the compound or pharmaceutically acceptable salt thereof and a pharmaceutically acceptable carrier suitable for oral, parenteral, or topical administration.

4. The method of claim 1, wherein the subject has osteoarthritis or aplastic anemia.

5. The method of claim 1, wherein the subject has Graves' disease.

6. The method of claim 1, wherein the subject is also administered one or more other bone marrow/stem cell stimulating agents.

7. The method of claim 6, wherein the bone marrow/stem cell stimulating agent is selected from a CXCR4 antagonist, plerixafor, vascular endothelial growth factor, granulocyte colony stimulating factor, filgrastim, pegfilgrastim, erythropoietin, and darbepoetin.

\* \* \* \* \*